United States Patent [19]

Nozaki

[11] 4,180,694

[45] Dec. 25, 1979

[54] PRODUCTION OF 1,7-OCTADIENE FROM BUTADIENE

[75] Inventor: Kenzie Nozaki, Houston, Tex.

[73] Assignee: Shell Oil Company, Houston, Tex.

[21] Appl. No.: 927,692

[22] Filed: Jul. 24, 1978

[51] Int. Cl.² ............................................. C07C 11/12
[52] U.S. Cl. ................................. 585/511; 252/431 P
[58] Field of Search ....................... 260/680 B, 680 R; 252/431 P

[56] References Cited

U.S. PATENT DOCUMENTS 3,732,328   5/1973   Wright .............................. 260/680 B

*Primary Examiner*—Delbert E. Gantz
*Assistant Examiner*—Joseph A. Boska
*Attorney, Agent, or Firm*—Howard W. Haworth

[57] ABSTRACT

Butadiene is hydrodimerized to 1,7-octadiene in high yield by contacting the butadiene with a formate of an alkali metal, alkaline earth metal or ammonia, a palladium catalyst, tertiary phosphine, a solvent selected from dialkyl sulfoxides, N,N-dialkylalkanamides, substituted and unsubstituted pyridines and sulfolanes and at least one mole of water per mole of formate salt.

16 Claims, No Drawings

PRODUCTION OF 1,7-OCTADIENE FROM BUTADIENE

BACKGROUND OF THE INVENTION

1. Field of the Invention

The present invention relates to the production of 1,7-octadiene by hydrodimerizing butadiene.

2. Description of the Prior Art

Linear dimerization of butadiene provides a source of $C_8$ unsaturated hydrocarbon intermediates useful for the synthesis of diacids, diesters, diols or diamines. A particularly preferred dimer is 1,7-octadiene which has terminal double bonds and allows the production of product having only terminal functional groups.

Several references disclose the use of formic acid as a reducing agent in the hydrodimerization of butadiene for example see Wright, U.S. Pat. No. 3,732,328, issued May 8, 1973; U.S. Pat. No. 3,832,199, issued July 9, 1974, British Pat. No. 1,341,324 issued Dec. 9, 1973; Gardner et al in *Tetrahedron Letters No. 2*, pp. 163164, and Roffia et al in *J. of Organometallic Chemistry*, 55 (1973) 405407.

Formic acid is frequently obtained commercially by the direct reaction of alkali and carbon monxide followed by acid hydrolysis of the resulting alkali formate. It would be of an economic advantage to utilize the alkali formate directly. None of the cited references teach the use of alkali formates to produce 1,7-octadiene in high yield.

SUMMARY OF THE INVENTION

It has been found that butadiene can be hydrodimerized to 1,7-octadiene in high yields by contacting the butadiene with a salt of formic acid and a strong inorganic base, a palladium catalyst, a tertiary phosphine, a solvent selected from dialkyl sulfoxides and N,N-dialkylalkanamides, substituted and unsubstituted pyridines and sulfolanes and at least one mole of water per mole of formate salt. Other solvents give much lower yields of 1,7-octadiene. A lack of water in the reaction mixtures lowers the yield of 1,7-octadiene and increases the yield to 1,6-octadiene.

DESCRIPTION OF THE PREFERRED EMBODIMENTS

The Palladium-Phosphine Complex

The palladium compounds used to form the catalyst utilized in this invention are those compounds of palladium which readily form complexes with triorganophosphines. These may be organic or inorganic compounds. Suitable palladium compounds include the palladium carboxylates, particularly palladium carboxylates derived from alkanoic acids containing up to six carbon atoms such as palladium acetate (OAC), complexes such as palladium acetylacetonate (AcAc), bisbenzonitrile palladium (II) and lithium palladous chloride as well as the palladium halides, nitrates and sulfates such as palladous chloride and palladium nitrate $(Pd(NO_3)_2(OH)_2)$ and palladium sulfate. A preferred catalyst species is palladium acetylacetonate. The palladium compound will be present in the reaction mixture in catalytic amounts; preferably from about 1 to about $10^{-6}$ molar and more preferably from $10^{-1}$ to about $10^{-4}$ molar. The palladium may be in any of its oxidation states, e.g., 0, +2. Suitable reduced palladium phosphine complexes are $Pd(R_3P)_2$ or $Pd(R_3P)_3$.

Any tertiary phosphine which can be dissolved in the reaction mixture may be used. The bisphosphines, such as 1,3-bis-phenylphosphinopropane and 1,4-bis-diphenylphosphinobutane, will not function in the present invention as the tertiary phosphine, the butadiene conversions obtained are unsatisfactory. Accordingly, it is preferred to use a mono-phosphine. Suitable phosphines are represented by the formula:

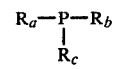

wherein $R_a$, $R_b$ and $R_c$ may be the same or different and are selected from aryl such as phenyl, p-tolyl, o-tolyl, m-tolyl, m-chlorophenyl, phenoxy, p-methylphenoxy, p-anisoly, m-anisoyl and the like, alkyl of 1 to 8 carbon atoms, preferably 1 to 5 carbon atoms, alkoxy having from 1 to 8 carbon atoms, but preferably from 1 to 3 carbon atoms. Preferably, $R_a$, $R_b$ and $R_c$ represent aryl, alkyl, or a mixture thereof having carbon numbers from 1 to about 12. The more preferred tertiary phosphines, are the triaryl and trialkyl phosphines. The most preferred tertiary phosphines have the following general formula

wherein $R_1$ is benzyl or branched alkyl, aralkyl, alkenyl, and cycloalkyl having from 3 to about 10 carbon atoms with branching occurring at a carbon atom no more than two carbon atoms from the phosphorus atom and $R_2$ and $R_3$ and $R_1$ or independently are alkyl, alkenyl or aryl having from 1 to about 10 carbon atoms.

Illustrative of the $R_1$ moiety are, for alkyl, isopropyl sec-butyl, tert-butyl, isobutyl, neopentyl, sec-pentyl, tertpentyl, 2-methylbutyl, sec-hexyl, tert-hexyl, 2,2-dimethylpropyl; for aralkyl, alpha-methylbenzyl, alpha,alpha-dimethylbenzyl, alpha-methyl-alpha-ethylbenzyl, phenylethyl, phenylisopropyl, phenyl-tert-butyl; for alkenyl allyl, crotyl, methallyl, 1-methylethenyl, 1-methyl-2-propenyl, 2-methyl-2-propenyl, 1,1-dimethyl-2-propenyl, 1-methyl-3-butenyl and, for cycloalkyl, cyclopropyl, cyclobutyl, cyclopentyl, cyclohexyl, cycloheptyl, and the like.

Illustrative of $R_2$ and $R_3$ are, for example, methyl, ethyl, propyl, butyl, pentyl, hexyl, octyl, nonyl and decyl for alkyl; allyl, crotyl and methallyl for alkenyl, and phenyl, tolyl, xylyl, ethylphenyl, propylphenyl for aryl. Two or more of the instant phosphines may be used in the same reaction. The mole ratio of tertiary phosphine to palladium is at least 1. Preferably the mole ratio of phosphine to palladium ranges from about 1:1 to about 1:20 and preferably from about 2:1 to about 5:1. The use of the phosphines of the invention provides extremely high selectivities to 1,7-octadiene.

Alternatively, the palladium compound and tertiary phosphine may be bound onto a crosslinked synthetic resin instead of being dissolved in the reaction medium. Acceptable crosslinked synthetic resins include crosslinked polystyrene, poly(alpha-alkyl) acrylates, polycarbonates, polyamides and the like.

The bound tertiary phosphine may have the general formula:

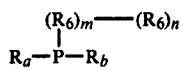

wherein $R_a$ and $R_b$ are defined previously, and $R_6$ represents the repeating unit of the synthetic resin and where m is a positive integer, n is 0 or a positive interger, m+n equal the total number of repeating units in resin and the percentage of the repeating units substituted with the tertiary phosphine is represented by the formula:

$$\frac{m}{m+n} \times 100\%$$

The number of repeating units substituted with the tertiary phosphine is not critical. When less than 5% of the repeating units contain a phosphine substitute, large quantities of the resin must be used to form the bound catalyst. Accordingly, it is desirable to have at least 10% of the repeating units substituted with a tertiary phosphine. It is preferred, however, that from 20 to 40% of the repeating units contain a phosphine substituent. The substituent can be introduced into the resin using well-known techniques, such as those described by Smith et al in the Journal of the American Chemical Society, 97 (7) 1749 (1975) and by Pittman et al in Ann. N.Y. Academy of Sciences, 239, 76 (1974). In accordance with those techniques, the palladium compound is complexed with the phosphine-substituted resin by admixing in a solvent for palladium acetate.

The palladium compound trisorgano phosphine complexes are typically prepared by reacting the tertiary phosphine with the appropriate palladium compound as, for example, represented by the following equations:

$2R_3P + (PhCN)_2PdCl_2 \rightarrow (R_3P)_2PdCl_2$

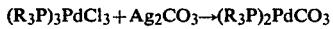

$(R_3P)_3PdCl_3 + Ag_2CO_3 \rightarrow (R_3P)_2PdCO_3$

$(R_3P)_2PdO_2 + SO_2 \rightarrow (R_3P)_2PdSO_4$

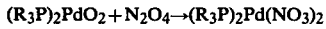

$(R_3P)_2PdO_2 + N_2O_4 \rightarrow (R_3P)_2Pd(NO_3)_2$ or may be made in situ by adding the palladium compound and the phosphine directly to the reactor.

The catalyst may be pretreated to enhance reactivity by contacting it with a reducing agent at a temperature of from about 20° to about 90° C. for from about 0.1 to about 5 hours. The reducing agent may be gaseous, solid or liquid. Examples of gaseous agents are hydrogen, and carbon monoxide. Examples of liquid or solid reducing agents are hydrazine, $NaNH_4$, $NaOCH_3$, (isopropyl)$_3$P, Cu, Na, Al alkyls, etc. A particularly preferred agent is the ammonium salt of formic acid which is utilized in the hydrodimerization reaction. The reduction may be carried out in a separate autoclave or preferably is carried out in the hydrodimerization reactor prior to the introduction of the butadiene. The palladium compound-tris-organophosphine complex may be dissolved in a solvent prior to reduction. The preferred solvents are those used in the hydrodimerization reaction described below.

The solvents needed to provide the higher yields of this invention are selected from the group consisting of dialkyl-sulfoxides, N,N-dialkylalkanamides and substituted and unsubstituted pyridines and sulfolanes. By dialkyl it is meant that the sulfur and nitrogen atoms are connected to two different carbon atoms. These may be separate alkyl groups or the same, i.e., a ring alkyl group, i.e., tetramethylene sulfoxide and N-methyl pyrrolidinone. The alkyl moieties have carbon numbers ranging from 1 to about 6. The substitutions on the pyridines and sulfolanes are preferably alkyl of $C_1$ to about $C_6$. Preferred solvents are methylsulfoxide and dimethylformamide.

The formic acid salts utilized in this invention are the formic acid salts of the alkali metals, the alkaline earth metals and ammonia. Preferred salts are sodium and potassium formate.

It is desirable that some formic acid salt be present during the entire course of the reaction. When operating the process batch-wise, this can be accomplished by adding a stoichiometric amount of formic acid salt initially, 1 mole of formic acid salt for every 2 moles of butadiene, or by continuously or periodically adding additional amounts of formic acid salt.

Water must be present in the reaction mixture in greater than trace amounts. Preferred moles of water are at least equal to the moles of formate salts. Typically the water will range from about 1 to about 5 moles of water per mole of formate salt.

The addition of carbon dioxide to the reaction system has been found to increase the extent of butadiene conversion, but does not affect the selectivity. When it is desired to use carbon dioxide to increase the conversion rate, the partial pressure of the $CO_2$ in the reaction system may be from about 10 to about 100 psia. Since carbon dioxide is a by-product of the process, it is possible to generate sufficient carbon dioxide in situ to enhance the conversion rates.

The process can be either continuous or batch. The reaction temperature of the process is not critical, however, it is preferred to maintain the reaction between about 0° to about 100° C. preferably between about 20° to about 70° C. The process is conducted under a sufficient pressure to maintain liquid phase conditions at the reaction temperature. Typically the pressure is autogeneous.

The process of this invention is particularly useful when applied to a BBB stream from an oil pyrolysis unit. These BBB streams are the $C_4$ cut from a thermal cracking unit typically containing 30–40% butadiene, 20–35% isobutene and 20–30% n-butenes and many minor components.

The process of this invention will be further described by the following illustrative embodiments which are provided for illustration and are not to be construed as limiting the invention.

ILLUSTRATIVE EMBODIMENTS

Illustrative Embodiment I

To an 80 milliliter glass-lined autoclave were charged $2.7 \times 10^{-5}$ moles of $Pd(NO_3)_2(OH)_2$, $1.85 \times 10^{-2}$ moles of sodium formate, in $5.4 \times 10^{-5}$ moles of triisopropylphosphine, 10 ml of the solvent listed in column 1 of Table 1, 0.4 g $H_2O$ and 2 grams of 1,3-butadiene. The stirred reactor was heated to 60° C. for 1 hour, cooled and the product was analyzed by gas chromatography for the amount of 1,7-octadiene present. The results are shown in column 2 in Table 1.

TABLE 1
SODIUM FORMATE AND SOLVENTS

| Solvent | Butadiene Converted to 1,7-Octadiene, % |
|---|---|
| Dimethylsulfoxide | 88 |
| Dimethylformamide | 87 |
| 1-Methyl-2-Pyrrolidinone | 59 |
| Methanol | 38 |
| Sulfolane | 37 |
| Pyridine | 12.5 |
| Methyl Formate | 12.3 |
| Ethanol | 11.2 |
| Acetone | 8.8 |
| Acetonitrile | 7.4 |
| Ethylene Carbonate | 4.3 |
| Tetrahydrofuran | 3.8 |
| Nitromethane | 1.8 |
| Ethylene Glycol | 0.5 |
| Formamide | 0.5 |
| Hexafluroisopropyanol | 0 |
| Acetic Acid | 0 |
| Liquid Ammonia | 0 |
| Liquid Sulfur Dioxide | 0 |
| 18-Crown-6 | 0 |

Illustrative Embodiment II

To an 80 milliliter glass-lined autoclave were charged $2.7 \times 10^{-5}$ moles $Pd(NO_3)_2(OH)_2$, $5.4 \times 10^{-5}$ moles triisopropyl phosphine, 10 ml of the solvent listed in columns 2 of Table 2, 0.4 g of $H_2O$, 2 g of butadiene and $1.85 \times 10^{-2}$ moles of the metal formate listed in column 1 of Table 2. The stirred reactor was heated to 60° C. for 1 hour, cooled and the product was analyzed by gas chromatography from the amount of 1,7-octadiene present. The results are shown in column 3 in Table 2.

TABLE 2
OTHER METAL FORMATES

| Metal Formate | Solvent | Butadiene Converted to 1,7-Octadiene, % |
|---|---|---|
| Lithium | Dimethylsulfoxide | 73 |
| Sodium | Dimethylsulfoxide | 88 |
| Potassium | Dimethylsulfoxide | 89 |
| Calcium | Dimethylsulfoxide | 80 |
| Ammonium (NO $H_2O$) | Dimethylsulfoxide | 80 |
| Lithium | Dimethylformamide | 51 |
| Sodium | Dimethylformamide | 87 |
| Potassium | Dimethylformamide | 35 |
| Calcium | Dimethylformamide | 48 |
| Lithium | Sulfolane | 14 |
| Sodium | Sulfolane | 37 |
| Potassium | Sulfolane | 2.8 |
| Calcium | Sulfolane | 0 |
| Lithium | Pyridine | 3.8 |
| Sodium | Pyridine | 12.5 |
| Potassium | Pyridine | 4.2 |

Illustrative Embodiment III

To an 80 milliliter glass-lined autoclave were charged the catalyst given in column 1 of Table 3, 10 ml of pyridine, various amounts of water and sodium formate and 2 g of butadiene. The stirred reactor was heated to various temperatures for 1 to 2 hours (given in columns 4 and 5), cooled and the product was analyzed by gas chromatography for the amount of 1,6- and 1,7-octadiene present. The results are shown in the last two columns.

TABLE 3
Conditions: 2 g Butadiene, 10 ml Pyridine

| Catalyst $\times 10^{-5}$ moles | $H_2O$ g | Sodium Formate, g | Time hrs. | Temp. °C | Conv. to 1.7$C_8$ % | Conv. to 1.6$C_8$ % |
|---|---|---|---|---|---|---|
| $Pd(OAc)_2$ (2.7) isopropyl$_3$P (10.8) | 0 | 0.20 | 2 | 60 | 7 | 24.5 |
| $Pd(OAc)_2$ (2.7) isopropyl$_3$P (10.8) | 0.1 | 0.20 | 2 | 60 | 99 | 1 |
| $Pd(OAc)_2$ (2.7) isopropyl$_3$P (10.8) | 0.4 | 1.25 | 2 | 60 | 89 | 1.5 |
| $Pd(OAc)_2$ (2.7) isopropyl$_3$P (5.4) | 0.4 | 1.25 | 1 | 60 | 77 | 1.5 |
| $Pd(OAc)_2$ (2.7) isopropyl$_3$P (5.4) | 0.7 | 1.25 | 1 | 60 | 71 | 2 |
| $Pd(\phi_3P)_4$ (2.7) | 0 | 1.25 | 1 | 75 | 0.2 | 2.3 |
| $Pd(\phi_3P)_4$ (2.7) | 0.4 | 1.25 | 1 | 75 | 4.8 | 0.6 |
| $Pd(\phi_3P)_4$ (2.7) + 0.5g NaOH | 0.4 | 1.25 | 1 | 75 | 0.18 | — |
| $Pd(\phi_3P)_4$ (2.7) + 0.5g NaOH + 100#$CO_2$ | 0.4 | 1.25 | 1 | 75 | 28.6 | 3.2 |
| $Pd(OAc)_2$ (2.7) isopropyl$_3$P (5.4) | 0.6 | 1.25 | 1 | 40(a) | 18.5 | 0.35 |
| $Pd Cl_2$ (2.7) isopropyl$_3$P (5.4) | 0.6 | 1.25 | 1 | 40(a) | 0.12 | 0.02 |

(a)Pretreated 1 hr. 75° C. before addition of butadiene.

Illustrative Embodiment IV

To an 80 milliliter glass-lined autoclave were charged $2.7 \times 10^{-5}$ moles of the catalyst listed in column 1 of Table 4, $5.9 \times 10^{-5}$ moles of triisopropylphosphine, 10 ml of the solvent listed in column 2, 0.4 g of water unless otherwise noted, $1.85 \times 10^{-2}$ moles of sodium formate and 2 g of butadiene. The stirred reactor was heated to 55° C. for 1 hour, cooled and the product analyzed by gas chromatography.

TABLE 4

| Pd Compound | Solvent | Butadiene Conv. to 1,7-Octadiene | Selectivity to 1,7-Octadiene |
|---|---|---|---|
| $Pd(NO_3)_2(OH)_2$ | Pyridine | 1.2 | — |
| $PdSO_4$ | Pyridine | 52 | 98.5 |
| $Pd(OAc)_2$(a) | Pyridine | 63 | 97 |

TABLE 4-continued

| Pd Compound | Solvent | Butadiene Conv. to 1,7-Octadiene | Selectivity to 1,7-Octadiene |
|---|---|---|---|
| Pd(AcAc)$_2$[a] | Pyridine | 64 | 98 |
| Pd(OAc)$_2$ | Nitromethane | 2.2 | 98 |
| Pd(OAc)$_2$ | Methanol | 2.4 | — |
| Pd(OAc)$_2$ | Acetone | 6 | 96 |
| Pd(OAc)$_2$ | Pyridine (1% H$_2$O) | 15 | 96 |
| PD(OAc)$_2$ | Pyridine | 63 | 97 |
| Pd(OAc)$_2$ | Sulfolane | 45 | 92 |
| Pd(OAc)$_2$ | Dimethyl Sulfoxide | 65 | 96 |
| Pd(OAc)$_2$ | Dimethylformamide | 75 | 97 |
| Pd(AcAc)$_2$ | Pyridine | 64 | 98 |
| Pd(AcAc)$_2$ | Dimethylformamide | 67 | 98 |
| Pd(AcAc)$_2$ | Dimethyl Sulfoxide (DMSO) | 60 | 98 |
| Pd(AcAc)$_2$ | DMSO (0.0g H$_2$O) | 0.4 | — |
| Pd(AcAc)$_2$ | DMSO (0.17g H$_2$O) | 23 | 97 |
| Pd(AcAc)$_2$ | DMSO (0.34g H$_2$O) | 41 | 97 |
| Pd(AcAc)$_2$ | DMSO (1.0g H$_2$O) | 61 | 97 |
| Pd(AcAc)$_2$ | DMSO (2.0g H$_2$O) | 32 | 92 |

[a]OAc = acetate
[b]ACAC = acetylacetonate

Illustrative Embodiment V

A zero-valent palladium complex was prepared according to the teachings of W. Kuran and A. Musco, *Inorganica Chimica Acta*, Vol. 12, 1975, pp. 187–193. 6.8×10$^{-6}$ Moles of Pd(O)-(tert-cyclohexyl phosphine)$_2$ complex 1.85×10$^{-2}$ moles of sodium formate, 10 ml of dimethylsulfoxide, 0.4 g of water and 2 g of butadiene were charged to an 80 milliliter glass-lined autoclave. The stirred reactor was heated to 60° C. for 1 hour, cooled and the product analyzed by gas chromatography. Conversion of butadiene to 1,7-octadiene was 55% with a 98% selectivity.

What we claimed is:

1. The process of hydrodimerizing butadiene to 1,7-octadiene which comprises contacting the butadiene with a formate of an alkali metal or ammonia, a palladium catalyst, a tertiary phosphine, a solvent selected from the group consisting of dialkyl sulfoxides, N,N-dialkylalkanamides, alkyl substituted and unsubstituted pyridines and sulfolanes and about at least 1 moles of water per mole of formate salt.

2. The process of claim 1 wherein the alkyl moiety has a carbon number ranging from 1 to about 6.

3. The process of claim 2 wherein the solvent is selected from the group consisting of dimethylsulfoxide, tetramethylene sulfoxide, dimethylformamide.

4. The process of claim 3 wherein the solvent is selected from the group consisting of dimethylsulfoxide and dimethylformamide.

5. The process of claim 1 wherein the temperature ranges from about 0° C. to about 100° C., the palladium ranges from about 10$^{-1}$ to about 10$^{-4}$ molar and the molar ratio of tertiary phosphine to palladium is at least 1.

6. The process of claim 1 wherein the butadiene is contained in a BBB stream from an oil pyrolysis unit.

7. The process of claim 1 wherein the palladium is zero-valent palladium selected from the group consisting of Pd(tertiary phosphine)$_2$ and Pd(tertiary phosphine)$_3$.

8. The process of hydrodimerizing butadiene to 1,7-octadiene which comprises contacting the butadiene with a formate of an alkaline earth metal, a palladium catalyst, a tertiary phosphine, a solvent selected from the group consisting of dialkyl sulfoxides, N,N-dialkylalkanamides, alkyl substituted and unsubstituted pyridines and about an least 1 mole of water per mole of formate salt.

9. The process of claim 8 wherein the alkyl moiety has a carbon number ranging from 1 to about 6.

10. The process of claim 9 wherein the solvent is selected from the group consisting of dimethylsulfoxide, tetramethylene sulfoxide, and dimethylformamide.

11. The process of claim 10 wherein the solvent is selected from the group consisting of dimethylsulfoxide and dimethylformamide.

12. The process of claim 8 wherein the temperature ranges from about 0° C. to about 100° C., the palladium ranges from about 10$^{-1}$ to about 10$^{-4}$ molar and the molar ratio of tertiary phosphine to palladium is at least 1.

13. The process of claim 8 wherein the butadiene is contained in a BBB stream from an oil pyrolysis unit.

14. The process of claim 8 wherein the palladium is zero-valent palladium selected from the group consisting of Pd(tertiary phosphine)$_2$ and Pd(tertiary phosphine)$_3$.

15. The process of hydrodimerizing butadiene to 1,7-octadiene which comprises contacting the butadiene with a formate of an alkali metal or ammonia, a palladium catalyst, a tertiary phosphine, N-methyl-2-pyrrolidinone and about at least 1 mole of water per mole of formate salt.

16. The process of hydrodimerizing butadiene to 1,7-octadiene which comprises contacting the butadiene with a formate of an alkaline earth metal, a palladium catalyst, a tertiary phosphine, N-methyl-2-pyrrolidinone and about at least 1 mole of water per mole of formate salt.

* * * * *